United States Patent [19]
Bonutti

[11] Patent Number: 5,329,924
[45] Date of Patent: Jul. 19, 1994

[54] SEQUENTIAL IMAGING APPARATUS

[75] Inventor: Peter M. Bonutti, Effingham, Ill.

[73] Assignee: Apogee Medical Products, Inc., Effingham, Ill.

[21] Appl. No.: 927,341

[22] Filed: Aug. 10, 1992

Related U.S. Application Data

[63] Continuation-in-part of Ser. No. 802,358, Dec. 4, 1991.

[51] Int. Cl.⁵ .................... A61B 6/00; A61B 5/055
[52] U.S. Cl. .................... 128/653.1; 128/653.2; 128/653.5; 378/208; 5/601; 5/624
[58] Field of Search .......... 128/653.1, 653.2, 653.5, 128/88.2; 5/601, 624; 324/318; 378/208

[56] References Cited

U.S. PATENT DOCUMENTS

| | | | |
|---|---|---|---|
| 1,239,146 | 9/1917 | Wantz | 5/601 |
| 2,801,142 | 7/1957 | Adams | 5/623 |
| 2,972,505 | 2/1961 | Weickgenannt | 5/623 |
| 3,025,397 | 3/1962 | Travis et al. | 378/208 |
| 3,124,328 | 3/1964 | Kortsch | 5/646 |
| 3,521,876 | 7/1970 | Smith . | |
| 3,528,413 | 9/1970 | Aydt | 5/647 |
| 3,766,384 | 10/1973 | Anderson | 5/601 |
| 4,050,355 | 9/1977 | Niskanen | 74/817 |
| 4,232,681 | 11/1980 | Tulaszewski . | |
| 4,256,112 | 3/1981 | Kopf et al. | 378/208 |
| 4,291,229 | 9/1981 | Patt . | |
| 4,323,080 | 4/1982 | Melhart | 5/650 |
| 4,407,277 | 10/1983 | Ellison | 128/882 |
| 4,562,588 | 12/1985 | Ruf | 128/882 |
| 4,616,814 | 10/1986 | Hardwood-Nash | 5/601 |
| 4,681,308 | 7/1987 | Rice | 5/601 |
| 4,717,133 | 1/1988 | Walsh et al. | 5/624 |
| 4,827,496 | 5/1989 | Cheney . | |
| 5,001,739 | 3/1991 | Fischer | 378/208 |
| 5,007,912 | 4/1991 | Albrektsson et al. | 128/882 |
| 5,078,140 | 1/1992 | Kwoh | 128/653.1 |

OTHER PUBLICATIONS

Shellock, "Patellofemoral joint abnormalities in athletes: Evaluation by kinematic magnetic resonance imaging", Top Magn. Reson Imaging 1991 pp. 71-95.

*Primary Examiner*—Ruth S. Smith
*Attorney, Agent, or Firm*—Tarolli, Sundheim & Covell

[57] ABSTRACT

For use in medical imaging, an indexing assembly provides repeatable indexing movement of a joint in predetermined angular increments between sequential index positions. Means are provided for limiting movement of the joint to the next selected index position without skipping any index positions. The apparatus is contained entirely within, for example, a primary imaging coil of an MRI apparatus, and is patient directed.

32 Claims, 11 Drawing Sheets

SEQUENTIAL IMAGING APPARATUS

RELATED APPLICATIONS

This application is a continuation-in-part of earlier filed co-pending application Ser. No. 07/802,358, filed Dec. 4, 1991 by Peter M. Bonutti and entitled Apparatus and Method for Use in Medical Imaging. The benefit of the earlier filing date of the aforementioned application Ser. No. 07/802,358 for all subject matter common with this application is hereby claimed.

BACKGROUND OF THE INVENTION

1. Technical Field

The present invention relates to medical imaging apparatus. More particularly, the present invention relates to apparatus for use in imaging body parts such as joints, in applications such as magnetic resonance imaging, CAT scanning, X-ray imaging, etc.

2. Description of the Prior Art

Human body parts such as joints can be imaged with magnetic resonance imaging apparatus, CAT scanners, X-ray machines, and other types of imaging apparatus. A typical medical imaging apparatus can image a joint such as a knee joint in almost any single orientation, limited only by the physical dimensions of the imaging device. However, a typical imaging apparatus is not capable of taking sequential images of a joint in predetermined selected orientations, in a repeatable manner. The various bones, cartilage, ligaments, etc., assume different positions and orientations when the joint is flexed or extended. Imaging a joint in only one orientation may not reveal defects or disease which is visible only in certain orientations of the joint. Also, imaging a joint in only one orientation does not allow a doctor to study the full range of motion of the joint. Accordingly, it would be desirable to provide apparatus allowing for sequential, repeatable imaging of a joint in predetermined selected orientations.

SUMMARY OF THE INVENTION

In one embodiment, the present invention is an indexing assembly for imaging a joint of a patient, the joint being movable into a plurality of different orientations. The indexing assembly includes an index member connected with the joint for movement with the joint. The index member has a plurality of sequential index positions. A blocking member is movable relative to the index member between a first position blocking movement of the index member out of any one of the sequential index positions and a second position not blocking movement of the index member. The joint is imaged with the index member in one index position and the blocking member in the first position. After the joint is imaged, the blocking member is moved to the second position to release the index member. The patient moves the index member to the next sequential index position. The indexing assembly includes limiting means for limiting movement of the index member to movement into the next one of the sequential index positions upon movement of the index member out of any one of the sequential index positions.

Almost all the parts of the indexing assembly, including the index member and the blocking member, are disposed inside the primary imaging coil and closely adjacent to the joint during imaging of the joint. The only parts remote from the joint are a release control member for engagement by the patient and a connecting member connecting the release control member with the blocking member.

In another embodiment of the invention, an indexing assembly is provided for indexing the knee joint through its range of motion about an axis parallel to the plane of the table. The patient lies on his back on the imaging table, with the knee raised up off the table. As the patient moves his foot up and down, the knee joint is flexed and extended through its range of motion. The indexing assembly is attached to the end of the imaging table. This allows the patient's foot to drop down below the top of the table, when the index assembly is moved to a low position. Thus, the knee joint can be moved through a greater range of motion than if the foot could not drop below the top of the table. Accordingly, the physician can image the knee joint through a greater range of motion. This provides substantial advantages as compared to prior art imaging in which the patient's entire body remains above the top of the imaging table.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 7 is a fragmentary sectional view with parts removed showing the relative positions of the plunger and cocking pin when the apparatus is in the locked condition;

FIG. 8 is a view similar to FIG. 7 showing the relative positions of the plunger and cocking pin when the apparatus is in the unlocked position;

FIG. 11A is a view similar to FIG. 11 showing the index assembly in a second index position;

DESCRIPTION OF PREFERRED EMBODIMENTS OF THE INVENTION

Figure 1:
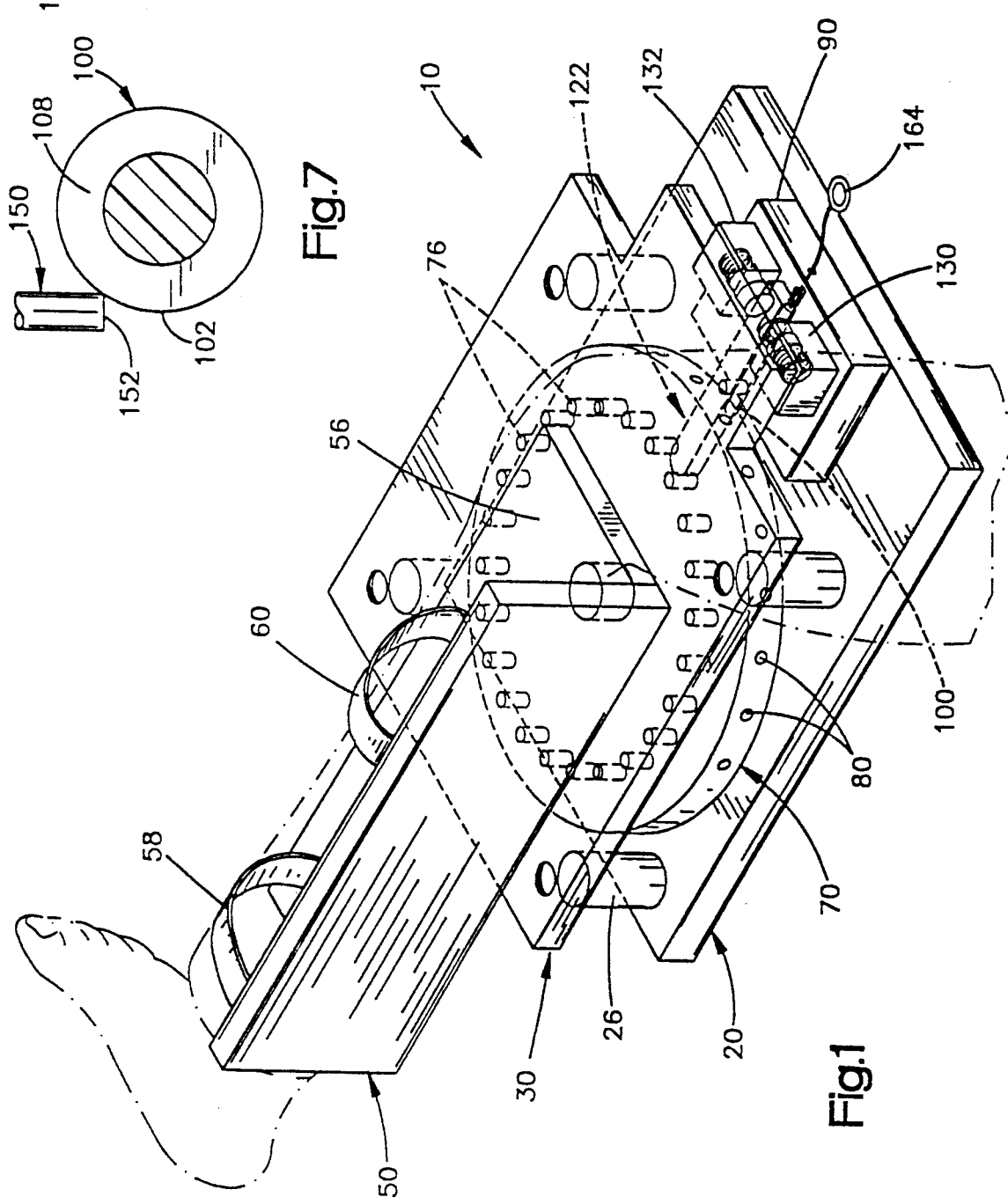
FIG. 1 is a perspective view of a sequential imaging apparatus in accordance with the present invention, showing a knee joint in position to be imaged.

The present invention relates to sequential imaging apparatus, and particularly to apparatus for sequential imaging of a joint in an imaging apparatus such as a magnetic resonance imaging apparatus. The present invention is applicable to various imaging apparatus constructions. As representative of the present invention, FIG. 1 illustrates an index assembly 10 for indexing movement of a knee joint in a direction parallel to the plane of an imaging table and about an axis normal to the plane of the imaging table.

Figure 14:
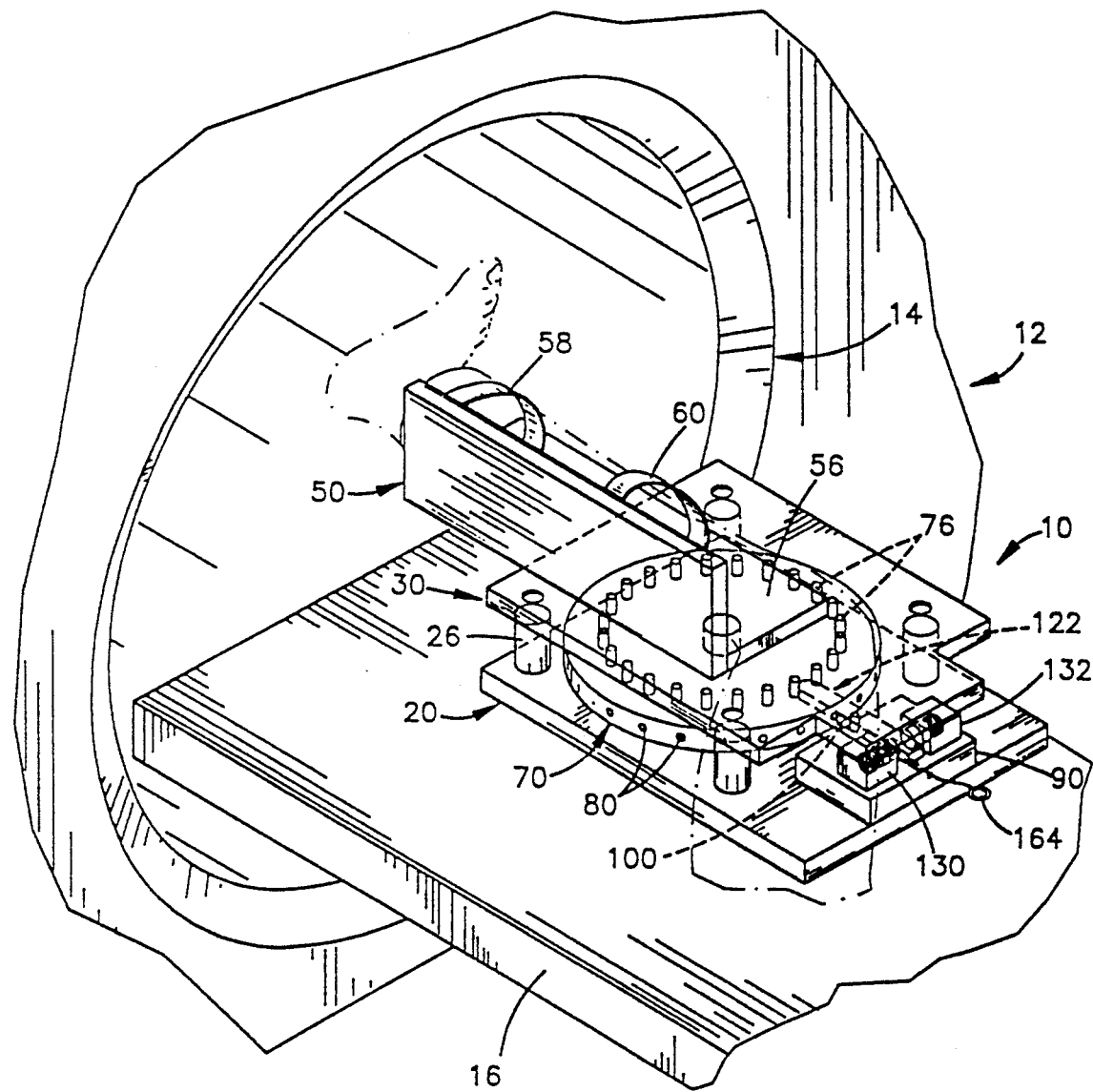
FIG. 14 is a perspective view of a magnetic resonance imaging apparatus in accordance with the present invention.

FIG. 14 schematically illustrates a known patient support table 16 for supporting a patient during imaging inside a known primary coil 14 of a known magnetic resonance imaging unit 12. The table 16 is supported for sliding longitudinal movement into an out of the primary coil 14 in a known manner. The index assembly 10 is positionable on the table for sliding longitudinal movement into and out of the primary coil 14.

Figure 2:
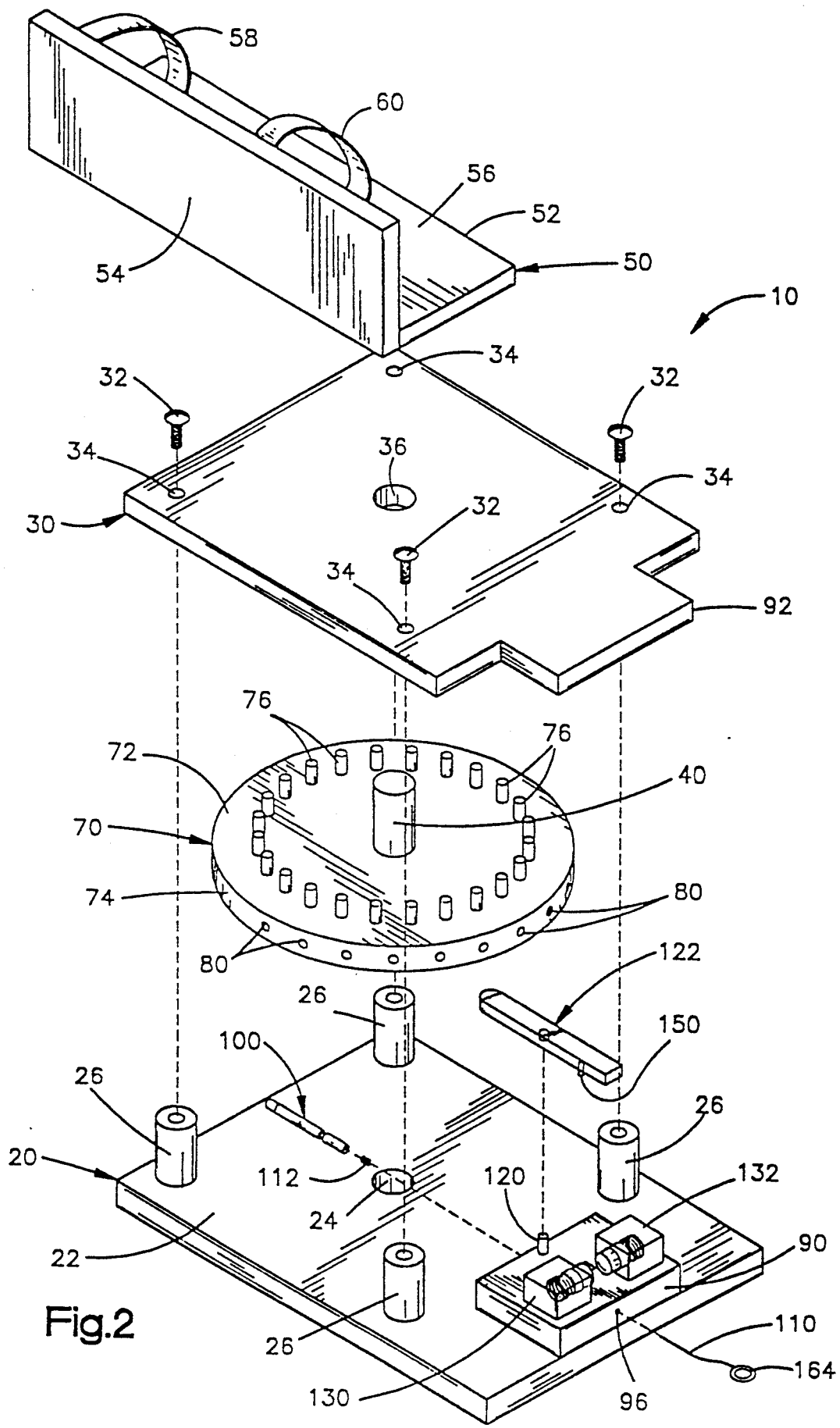
FIG. 2 is an exploded perspective view of the imaging apparatus of FIG. 1.

The index assembly 10 includes a generally planar base 20 having an upper major side surface 22 (FIG. 2). An opening 24 extends downwardly into the base 20 from the upper major side surface 22 of the base.

Four risers 26 are fixed to the base 20 and project upwardly from the upper major side surface 22 of the base. The risers 26 support a generally planar upper panel 30 at a location spaced from and parallel to the base 20. Four screws 32 extend through openings 34 in the upper panel 30 and into the risers 26, to secure the upper panel 30 to the base 20. An opening 36 extends through the upper panel 30. The opening 36 is coaxial with the opening 24 in the base 20.

Figure 4:
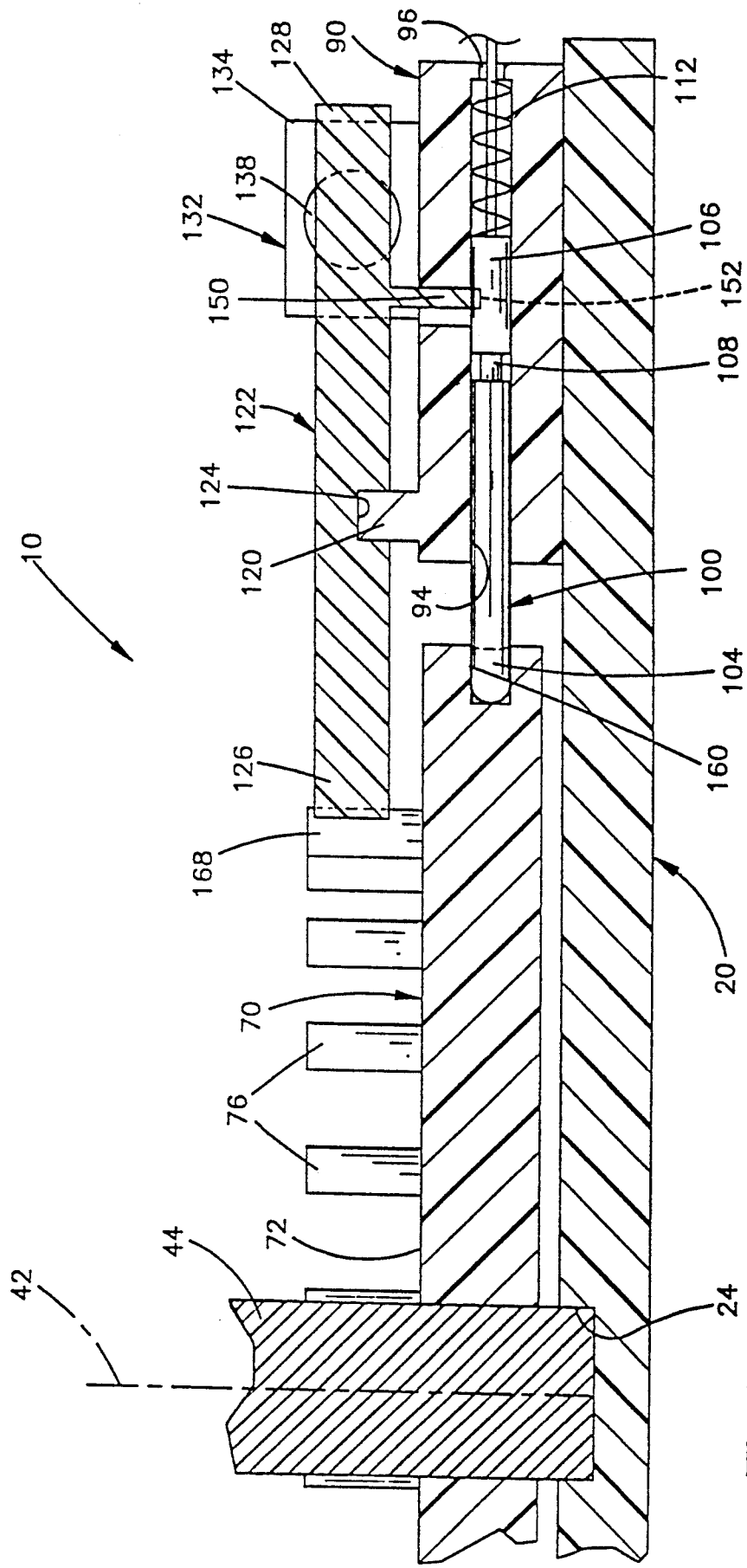
FIG. 4 is a fragmentary sectional view with parts removed showing portions of the imaging apparatus in a locked condition.
Figure 5:
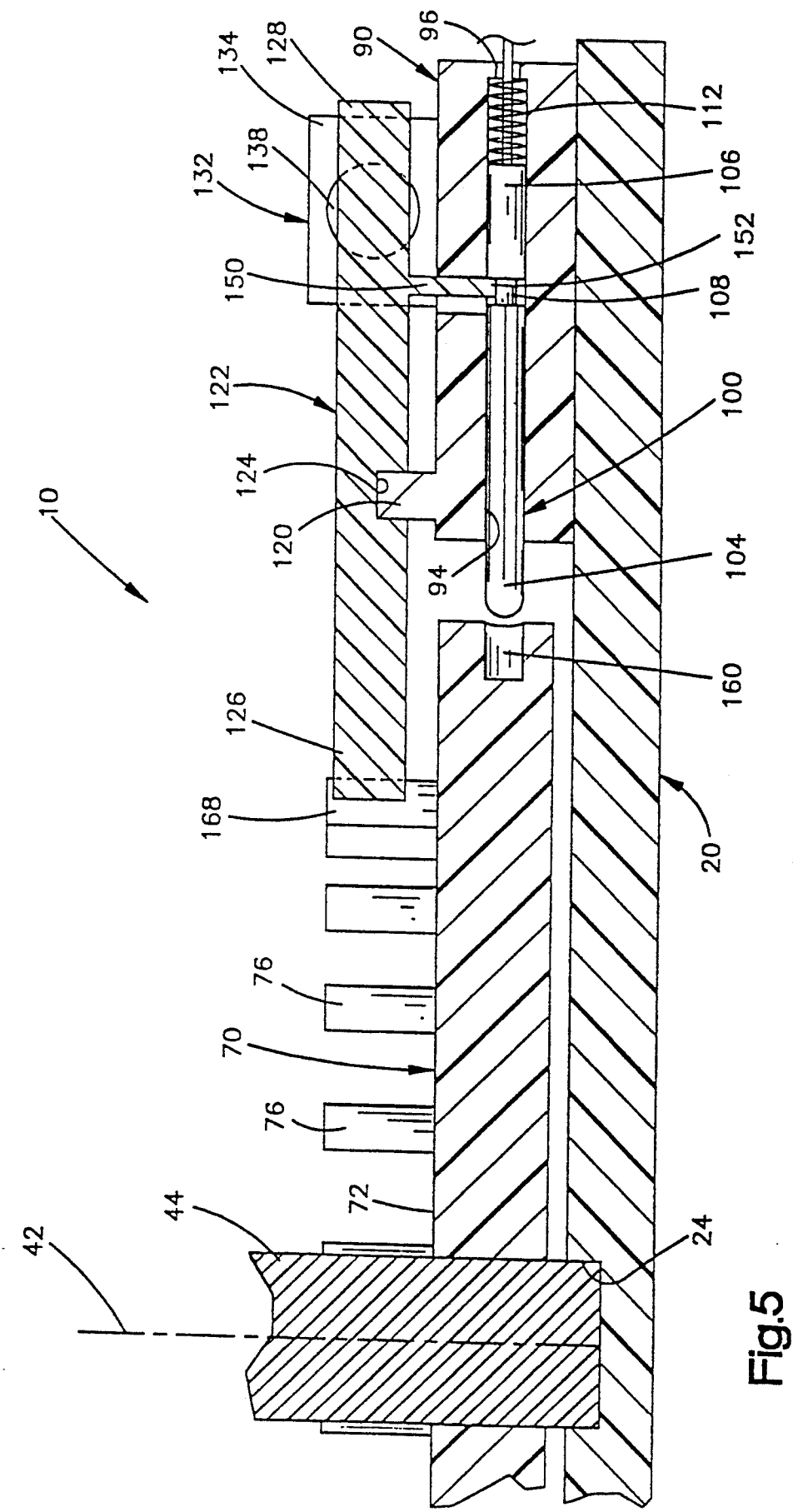
FIG. 5 is a view similar to FIG. 4, showing the imaging apparatus in an unlocked condition.

A central support shaft 40 has its lower end received in the opening 24 of the base 20 and its upper end extending through the opening 36 in the upper panel 30. The central support shaft 40 is rotatable relative to the base 20 and to the upper panel 30 about an axis 42 (FIGS. 4 and 5).

A tray 50 (FIG. 2) is fixed, in any suitable manner, to the upper end of the central support shaft 40. The tray 50 is rotatable with the central support shaft 40, relative to the base 22 and the upper panel 30. The tray 50 has a horizontal tray portion 52 and a vertical tray portion 54 fixed to each other. The horizontal tray portion 52 has an upper major side surface 56. Two leg straps 58 and 60 are fixed to the tray 50.

An index disk 70 is fixed for rotation with the central support shaft 40. The index disk 70 is cylindrical in shape and has a flat upper major side surface 72 and a cylindrical outer side surface 74.

A plurality of trip pins 76 are disposed in a circular pattern on the index disk 70 about the axis 42. The trip pins 76 extend upwardly from the upper major side surface 72 of the index disk 70. The radial distance from the axis 42 to each trip pin 76 is the same. All of the trip pins 76 are of the same dimensions and configuration. Thus, as the index disk 70 rotates about the axis 42, the trip pins 76 revolve in one circular path about the axis 42. The radially outermost surfaces of the trip pins 76 describe a circular path 78 indicated in dashed lines in FIGS. 3 and 6.

The trip pins 76 are spaced about the axis 42 in equal angular increments. In the illustrated embodiment, twenty-four trip pins 76 are provided, with an angular spacing of 15° between each trip pin. However, a different number of trip pins 76 can be provided, with correspondingly different spacing therebetween, as described below in greater detail.

Figure 3:
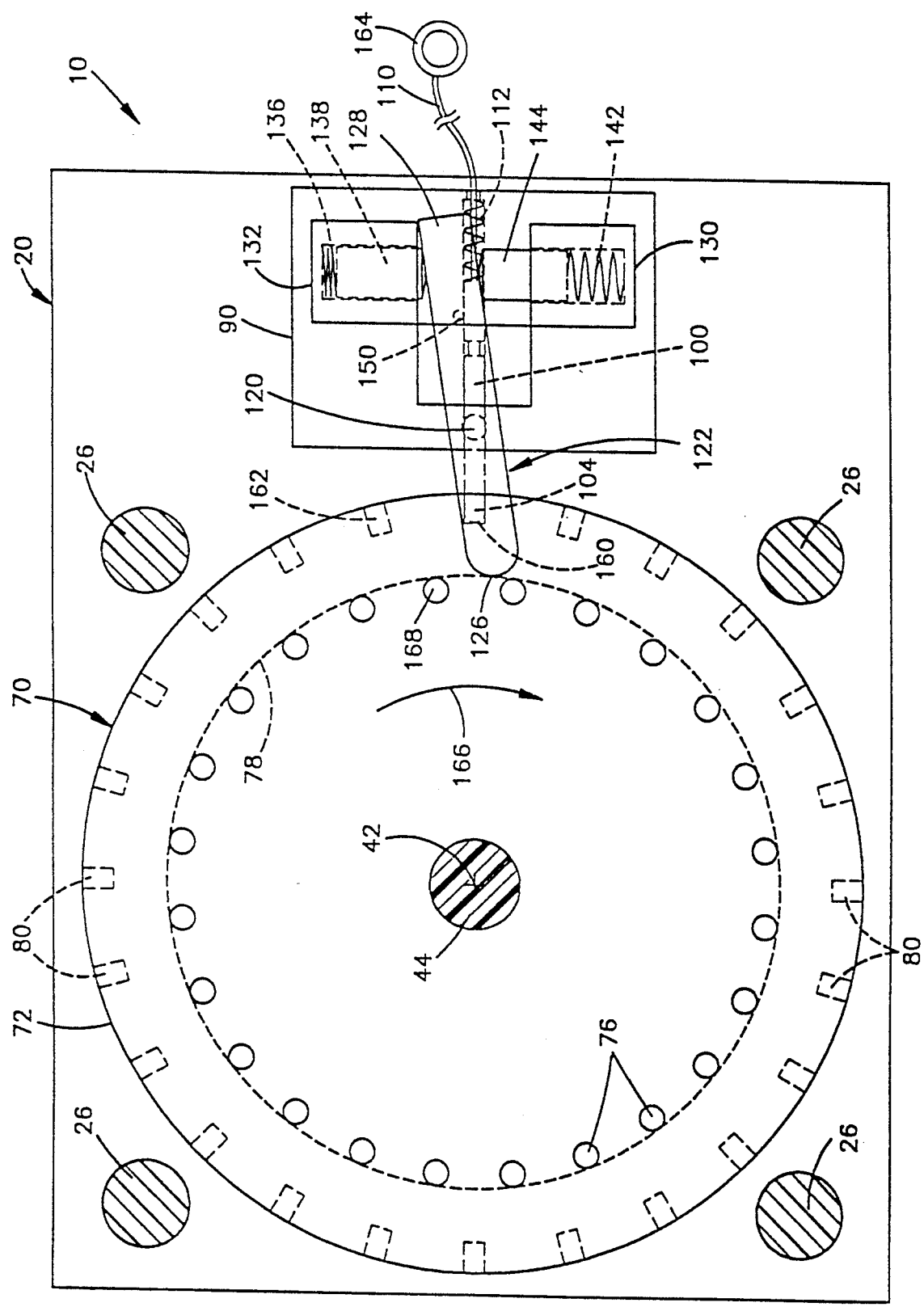
FIG. 3 is a top plan view with parts removed of the imaging apparatus of FIG. 1 in a locked condition.
Figure 6:
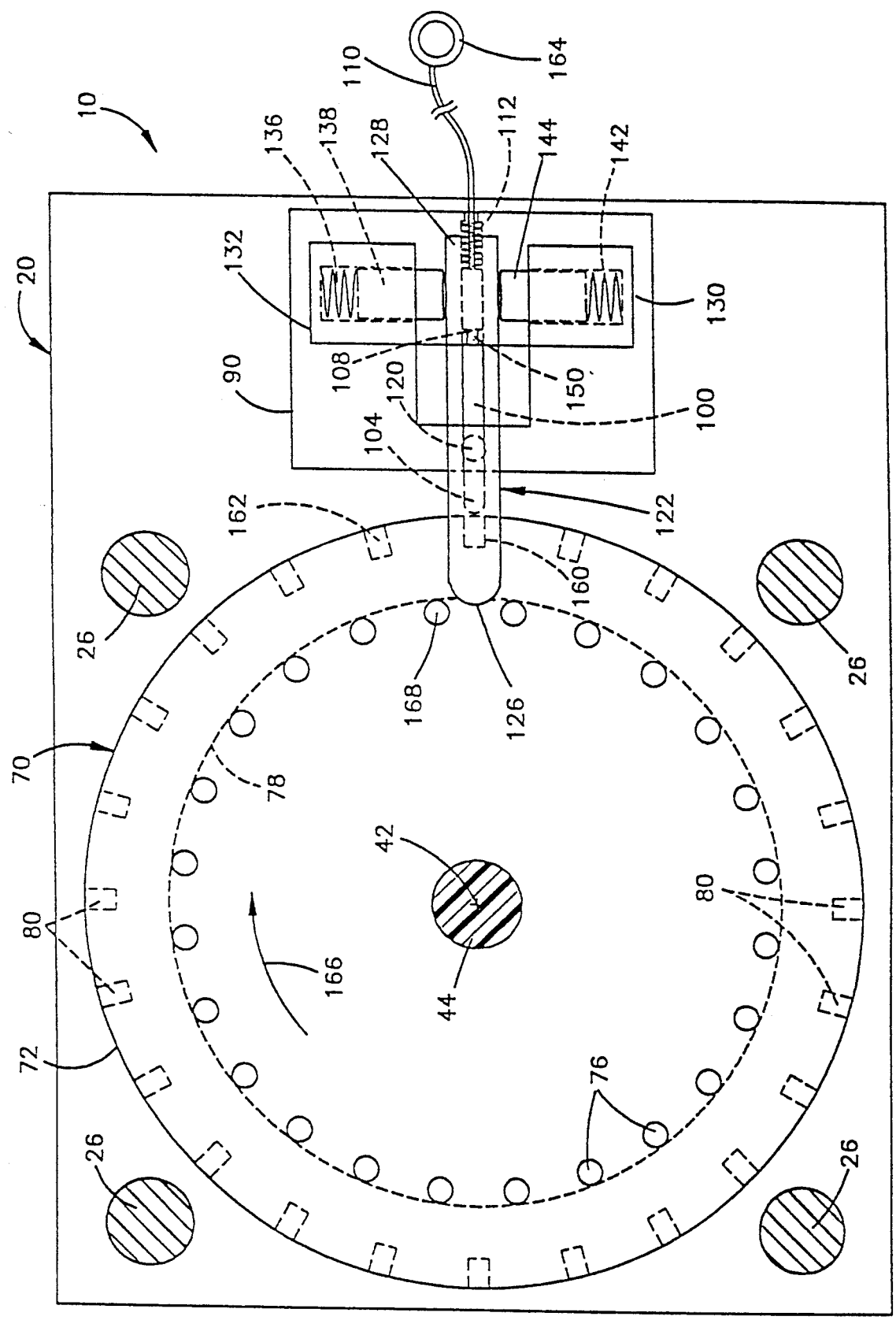
FIG. 6 is a view similar to FIG. 3 showing the imaging apparatus in an unlocked condition.

A plurality of index openings 80 in the index disk 70 extend radially inwardly from the cylindrical outer side surface 74 of the index disk for a relatively short distance toward the axis 42. There are as many index openings 80 as there are trip pins 76. The angular spacing between the index openings 80 is the same as the angular spacing between the trip pins 76. Thus, in the illustrated embodiment, twenty-four index openings 80 are provided, each spaced 15° apart from the next, around the outer circumference of the index disk 70. As can be seen in FIGS. 3 and 6, the index openings 80 are staggered relative to the trip pins 76. The index openings 80 are spaced circumferentially equidistant between pairs of adjacent trip pins 76.

A support block 90 is fixed to the base 20 at a location spaced from the index disk 70. An end portion 92 (FIG. 2) of the upper panel 30 projects over the support block 90. A cylindrical plunger opening 94 (FIG. 4) extends through the support block 90 in a direction to intersect the axis 42. The support block 90 has a reduced diameter neck portion 96 at the outer end of the plunger opening 94.

A plunger 100 is slidably received in the plunger opening 94 in the support block 90. The plunger 100 has a cylindrical outer surface 102 (FIGS. 7 and 8). The plunger 100 has a head end portion 104 (FIG. 4) and a trailing end portion 106. An annular groove 108 in the plunger 100 is disposed between the head end portion 104 and the trailing end portion 106.

An elongate member 110 (FIG. 3) is connected to the trailing end portion 106 of the plunger 100. The elongate member 110 (preferably a cord or a string) extends longitudinally through a compression spring 112 (FIGS. 3 and 4) disposed between the trailing end portion 106 of the plunger 100 (FIG. 4) and the support block neck portion 96. The spring 112 biases the plunger 100 relative to the support block 90 in a direction to the left as viewed in FIGS. 3–6, toward the index disk 70.

A swivel pin 120 is fixed to and extends upwardly from the support block 90. The swivel pin 120 (FIG. 4) is received in an opening 124 in a trigger 122. The swivel pin 120 supports the trigger 122 for pivotal movement about the swivel pin relative to the base 20.

The trigger 122 has a head end portion 126 which extends over the index disk 70. The head end portion 126 of the trigger 122 extends over the index disk 70 to a location radially inwardly of the path 78 defined by the radially outermost surfaces of the trip pins 76. Thus, as the index disk 70 rotates, the head end portion 126 of the trigger 122 is engageable by the trip pins 76.

A trailing end portion 128 of the trigger 122 extends between opposed trigger biasing assemblies 130 and 132. The trigger biasing assembly 132 (FIGS. 3 and 6) includes a housing 134 (FIGS. 4 and 5) fixed to the support block 90. A biasing block 138 (FIG. 3) is received in a cylindrical opening in the housing 134. A compression spring 136 biases the biasing block 138 against the trailing end portion 128 of the trigger 122, in a direction toward the bottom of FIGS. 3 and 6. Similarly, the biasing assembly 130 includes a compression spring 142 which urges a biasing block 144 in the opposite direction against the trailing end portion 128 of the trigger 122, that is, toward the top of FIGS. 3 and 6. The biasing effects placed on the trigger 122 by the biasing assemblies 130 and 132, respectively, are equal, so that the trigger 122 normally maintains the position illustrated in FIG. 6 aligned with the axis 42 and with the plunger 100.

The trigger 122 includes a cocking pin 150. The cocking pin 150 extends downwardly from the trailing end portion 128 of the trigger. The cocking pin 150 extends downwardly far enough so that as the trigger 122 pivots about the swivel pin 120, the cocking pin 150 can engage the outer side surface 102 of the plunger 100, as seen in FIG. 7. The lower end 152 of the cocking pin 150 can enter the groove 108 in the plunger 100, as seen in FIG. 8.

The index assembly 10 is adapted for imaging of the knee joint of a patient lying on a table inside a primary imaging coil of a magnetic resonance imaging apparatus. The patient supinates the foot and leg so that the lower leg fits along the upper major side surface 56 of the horizontal tray portion 52 of the tray 50, as illustrated in FIG. 1. The straps 58 and 60 are placed around the lower leg to stabilize the limb and secure the lower leg to the tray 50.

The index assembly 10 is initially in a locked condition as illustrated in FIGS. 3 and 4. One index opening 160 of the index openings 80 is aligned with the plunger 100. The spring 112 biases the head end 104 of the plunger 100 into the index opening 160. The plunger 100 blocks rotation of the index disk 70 about the axis 42. Because the index disk 70 cannot rotate, the central support shaft 42 and the tray 50 also cannot rotate. Thus, the patient's lower limb, which is strapped to the tray 50, is stabilized and a clear image of the knee joint can be taken.

When the index assembly 10 is in the locked condition shown in FIGS. 3 and 4, the trigger 122 is in a pivoted orientation not pointing toward the axis 142 and not parallel to the plunger 100. The cocking pin 150 of the trigger 122 extends below the top of the plunger 100. The cocking pin 150 engages along the cylindrical outer side surface 102 of the plunger 100, as illustrated in FIG. 3 and in more detail in FIG. 7. The plunger 100 holds the cocking pin 150 and the trigger 122 in this pivoted position illustrated in FIG. 3, against the biasing effect of the spring 136.

When it is desired to index the knee joint in a different orientation, the index assembly 10 must be released to allow the index disk 70 to move to the next index position. The patient pulls a handle 164 attached to the elongate member 110 extending from the plunger 100. The plunger 100 is retracted against the bias of the spring 112, from the blocking position illustrated in FIGS. 3 and 4 to the position illustrated in FIGS. 5 and 6. The head end portion 104 of the plunger 100 is retracted out of the index opening 160. The index disk 70 is then free to rotate if the patient moves the joint.

When the plunger 100 is retracted by the patient, the groove 108 in the plunger moves into a position adjacent the cocking pin 150. The cocking pin 150 is then free to move laterally into the groove 108 in the plunger 100. The biasing effect of the spring 136 pivots the trigger 122 so that the cocking pin 150 moves into the groove 108 of the plunger 100, centered over the plunger. The trigger 122 is in a cocked position. The springs 136 and 142 hold the trigger 122 centered between them, and the index assembly 10 is then in the position shown in FIGS. 5, 6, and 8. The engagement of the cocking pin 150 in the groove 108 of the plunger 100 blocks movement of the plunger 100 in a direction toward the index disk 70. The patient can release the handle 164, and the plunger 100 will not move into engagement with the index disk 70 or into any of the index openings 80.

The patient can then move the knee joint toward the next sequential index position at which an image is to be taken. As the patient flexes or extends the knee joint, the limb portion strapped to the tray 50 moves the tray 50 and causes the index disk to rotate, for example, in the direction indicated by the arrow 166 in FIG. 3. As the index disk 70 rotates, the trip pin closest to the trigger 122, which is the trip pin designated 168 in FIG. 3, engages the head end portion 126 of the trigger 122. The trip pin 168 pivots the trigger 122 about the swivel pin 120, from the cocked position illustrated in FIGS. 5 and 6 back toward the uncocked position illustrated in FIGS. 3 and 4.

When the trigger 122 pivots, the cocking pin 150 moves out of the groove 108 in the plunger 100, from the position illustrated in FIG. 8 to the position illustrated in FIG. 7. When the cocking pin 150 moves out of the groove 108 in the plunger 100, the plunger is then free to move longitudinally in the plunger opening 94 in the support block 90. The biasing effect of the plunger spring 112 causes the plunger 100 to move toward the index disk 70. The head end portion 104 of the plunger 100 engages the cylindrical outer side surface 74 of the index disk 70. As the index disk 70 continues to rotate in the direction indicated by the arrow 166, the next sequential index opening 162 moves into position between the axis 42 and the plunger 100, and the head end portion 104 of the plunger moves into the index opening 162, blocking further rotation of the index disk 70.

Rotation of the index disk 70 by the patient results in almost immediate engagement of the trigger 122 by the trip pins 76. This engagement releases the plunger 100, again almost immediately, and the plunger 100 is in position to engage the next succeeding index opening 80 along the outer circumferential surface 74 of the index disk 70. Thus, the construction of the index assembly 10 assures that whenever the patient releases the index assembly 10 by pulling on the handle 164, and then moves his knee joint, the index assembly 10 will lock in a next index position a given number of degrees from the previous index position. In the illustrated embodiment, that number of degrees is 15°. That number of degrees can be changed by placing the index openings 80 and the trip pins 76 at different angular spacings around the index disk 70. For example, if seventy-two trip pins 76 are provided, spaced 5° apart, and an equal number of index openings 80, then the movement of the index disk will be automatically limited to 5° of indexing each time. Thus, no matter how fast the patient flexes or extends his leg to rotate the index disk 70, the plunger 100 will always engage in the next sequential index opening 80 in the index disk 70. This assures that a precise repeatable sequence of images can be taken using the index assembly 10.

In the illustrated embodiment, the index assembly 10 is used in a magnetic resonance imaging application. Therefore, all of the parts of the index assembly 10 are made of nonferromagnetic materials. Preferably, the majority of the parts of the index assembly 10 are made of polyethylene or of Delrin ® brand plastic. The plunger spring 112 and the trigger biasing springs 136 and 142 can be made of beryllium copper or of a similar nonferromagnetic material having the desired spring characteristics. The straps 58 and 60 for stabilizing the patient's leg to the tray 50 can be made of nylon with suitable fasteners such as Velcro ® brand fasteners. The elongate member 110 can be a simple string or cord made of fabric or plastic.

It should be understood that the present invention is not limited to imaging of a knee joint, and that the present invention is not limited to imaging in a magnetic resonance imaging apparatus. The principles of the illustrated indexing assembly are applicable to imaging of almost any joint. Thus, the indexing assembly 10 can be configured to support other joints such as an elbow joint, an ankle joint, a wrist joint, or a shoulder joint. Sequential imaging of all these joints can be useful. An indexing assembly in accordance with the present invention can also be used in conjunction with a CAT scanner, an X-ray imaging apparatus, or other types of imaging apparatus.

It can thus be seen that the present invention provides an index assembly 10 for imaging a joint of a patient movable into a plurality of different orientations. The index assembly 10 includes an index disk 70 connected for movement with the joint by the tray 50. The index assembly 10 has a plurality of sequential index positions, two of which are illustrated in FIGS. 3 and 6. A plunger 110 is movable relative to the index disk 70 between a first position (illustrated in FIG. 3) blocking movement of the index disk out of any one of the sequential index positions, and a second position (illustrated in FIG. 6) not blocking movement of the index disk out of any one of the sequential index positions. An actuator 110, 164 is connected to the plunger 100 for moving the plunger between the first position and the second position. The index assembly includes trip pins 76 and a trigger 122 for limiting movement of the index disk 70 to movement into the next one of the sequential index positions upon movement of the index disk out of any one of the sequential index positions.

It can further be seen that the present invention contemplates that the entire index assembly 10 is disposed inside a primary imaging coil of a magnetic resonance imaging apparatus or the like in a location closely adjacent to a joint during imaging of the joint. The only parts remote from and not closely adjacent to the joint during imaging of the joint are a release control member or handle 164 and an elongate connecting member 110 connecting the release control member with the plunger 100. These parts are also within the primary imaging coil as they are grasped by the patient's hand.

It can be further seen that the present invention provides an actuator 164, 110 operable by a patient and connected to the plunger 100 for moving the plunger 100 into a position to allow movement of the index disk 70 out of a sequential index position, subsequent to imaging of a joint. The index assembly further includes a tray 50 and a central support shaft 40 for transmitting the force of movement of the joint between different orientations to the index disk 70 to move the index disk into the next one of its sequential index positions upon movement of the joint into a different orientation. Limiting means including the trigger 122 is operable to move the plunger 100 back into its locking position in one of the index openings 80, to allow imaging of the joint in the next one of its different orientations.

In a second embodiment of the invention, an indexing assembly is provided for movement of the knee joint about an axis parallel to the plane of an imaging table and in a direction transverse to the plane of the table. The patient lies on his back inside a primary imaging coil of a magnetic resonance imaging apparatus, and moves his lower leg up and down to extend and flex the knee joint. The knee is elevated so that the knee joint can be moved through its full range of motion.

Figure 9:
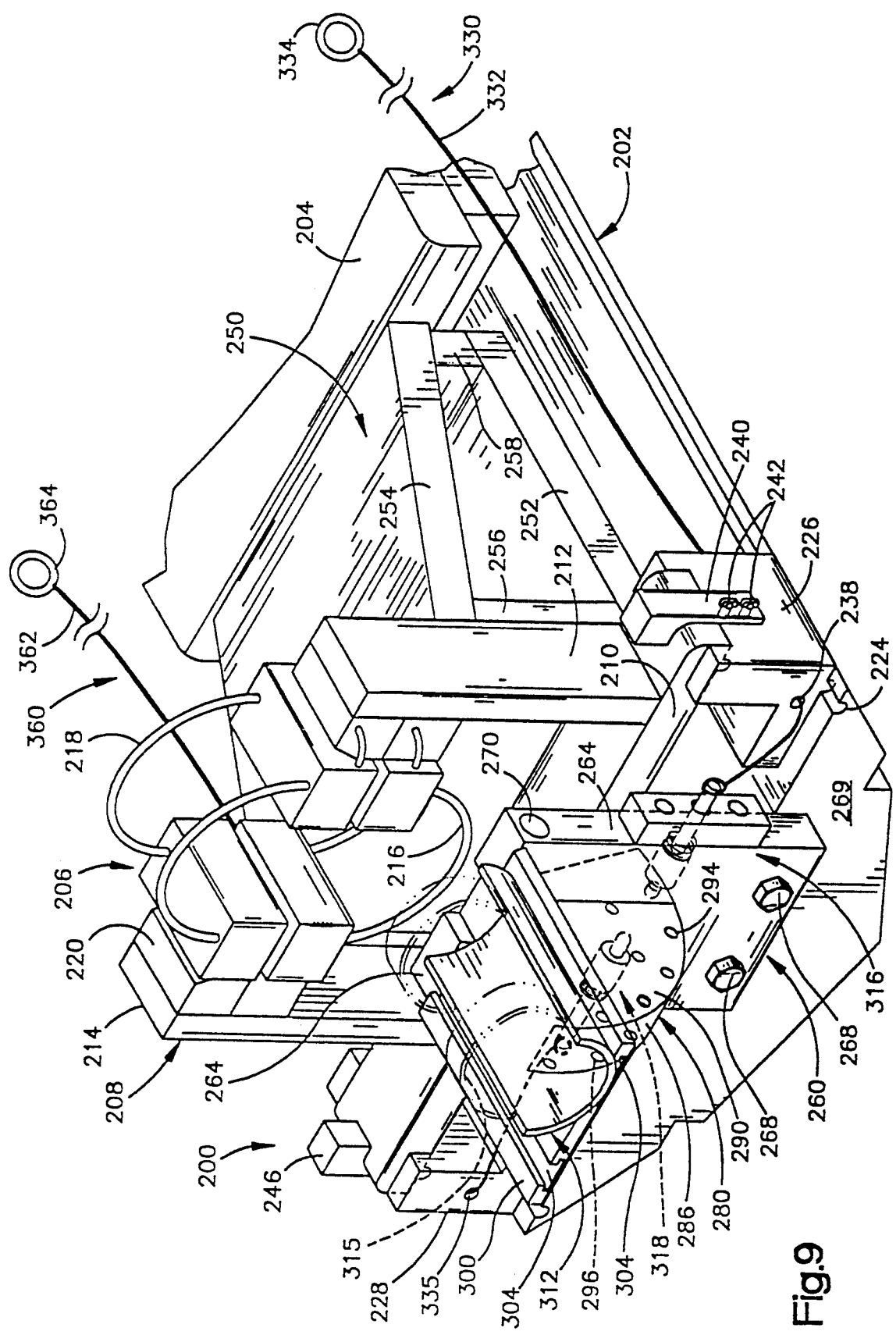
FIG. 9 is a perspective view of an imaging apparatus and index assembly in accordance with a second embodiment of the invention.
Figure 10:
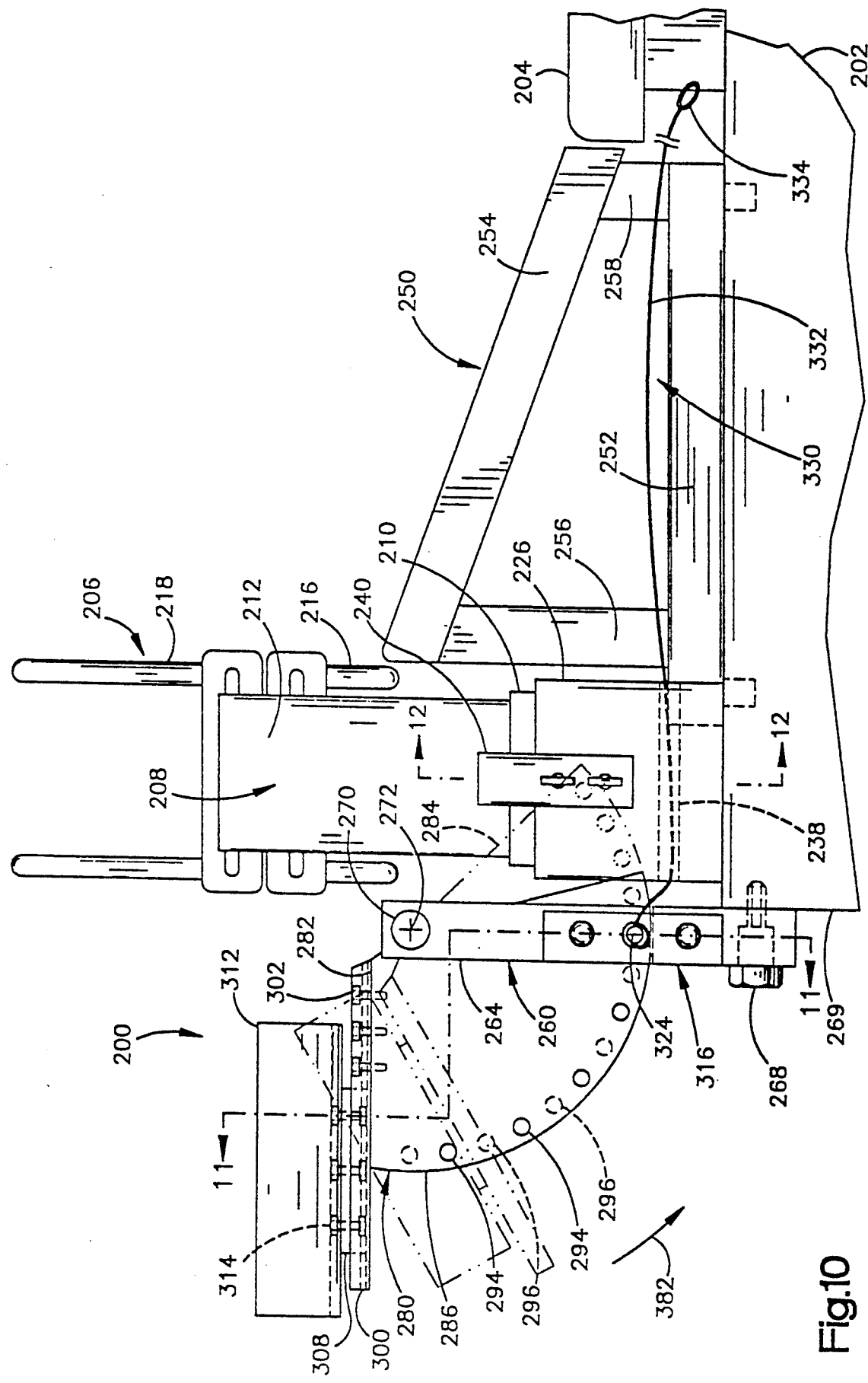
FIG. 10 is a side elevational view of the apparatus of FIG. 9 showing the index assembly in first and second index positions.

An index assembly 200 in accordance with the second embodiment of the invention is illustrated in FIGS. 9–13. FIGS. 9 and 10 show portions of an imaging table 202 which is slidable inside a primary coil (not shown) of a magnetic resonance imaging apparatus. The table 202 has an upper major side surface 203. The patient lies on a pad 204 on the table 202. The patient's head is towards the right as viewed in FIGS. 9 and 10. The table 202, with the pad 204, is movable longitudinally in and out of the primary coil. The table 202 is slid out to set up and place the patient on the table, then is slid in for imaging.

In addition to the primary coil, a known secondary coil assembly 206 may be used to obtain a better image of the knee joint. The secondary coil assembly 206 includes a frame 208 with a lower frame portion 210 and two upright frame portions 212 and 214. The secondary coil itself includes a lower coil portion 216 fixed to the coil frame 208. An upper coil portion 218 is pivotally mounted at one end 220 to the frame 208. The upper coil portion 218 is pivotable from the closed position shown in FIGS. 9 and 10 to an open position (not shown) to allow the patient's leg to be placed inside the secondary coil from above. The upper coil portion 218 then is swung back to the closed position to image the knee joint.

The coil lower frame portion 216 (FIG. 12) has on its lower surface a rib 222 which extends parallel to the length of the table 202. The rib 222 normally fits in a complementary groove 224 on the table 202, so that the secondary coil assembly 206 is slidable along the table 202 to image at various locations along the table. However, in accordance with the present invention, the knee is raised up off the table 202 to allow imaging of the knee joint through its range of motion. Thus, the secondary coil assembly 206 must also be raised up off the table 202.

A pair of coil support blocks 226 and 228 support the secondary coil assembly 206 in its raised position. Each coil support block has on its lower surface a rib 230 which fits into the groove 224 on the table 202. Each coil support block 226, 228 also has on its upper surface a groove 232 which accepts the rib 222 of the coil lower frame portion 216. Thus, the coil support blocks 226 and 28 and the secondary coil assembly 206 are slidable along the table 202 to image at various locations along the table. Each coil support block 226, 228 has a fastener opening 234 for receiving therethrough a suitable fastener (not shown) to secure the coil support block to an existing opening 236 in the table 202. Each coil support block 226, 228 also has an actuator passage 238 extending longitudinally through the coil support block in a direction parallel to the length of the table 202, for a purpose to be described below.

A coil clip 240 attaches the secondary coil assembly 206 to the coil support block 226. A pair of thumb screws 242 fix the coil clip 240 to the coil support block 226. A similar coil clip 246 holds the other end of the coil assembly 206 to the other coil support block 228.

A leg support wedge 250 raises the patient's knee so that it fits within the raised secondary coil assembly 206. The leg support wedge 250 includes a lower wedge member 252, an upper wedge member 254, and two wedge uprights 256 and 258. The lower wedge member 252 is disposed on the table 202. The wedge uprights 256 and 258 support the upper wedge member 254, at an angle, raised up from the lower wedge member 252. Thus, as the patient lies on the pad 204 on the table 202, the leg support wedge 250 raises the patient's knee so that it fits within the secondary coil assembly 206.

Figure 11:
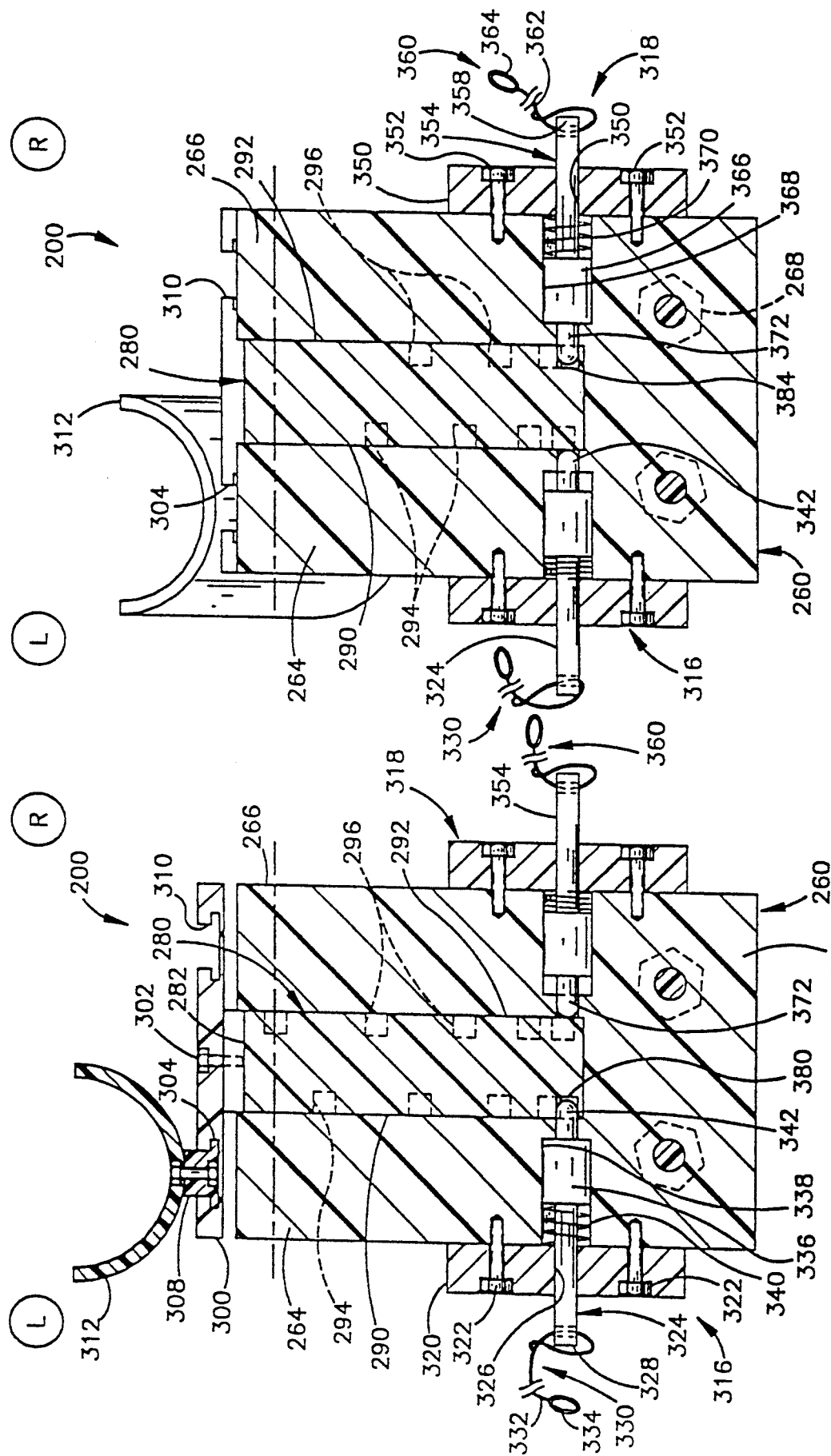
FIG. 11 is a sectional view taken along line 11—11 of FIG. 10 with parts removed, showing the index assembly in a first index position.
Figure 12:
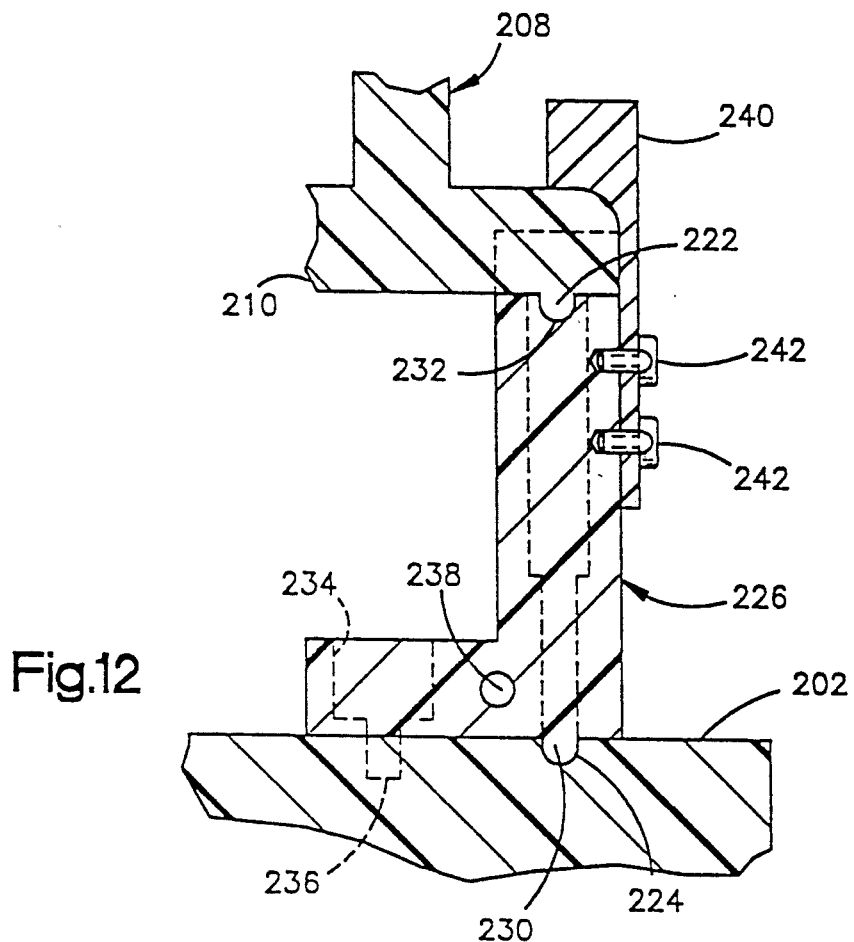
FIG. 12 is an enlarged fragmentary sectional view of a coil support portion of the apparatus of FIG. 9.
Figure 13:
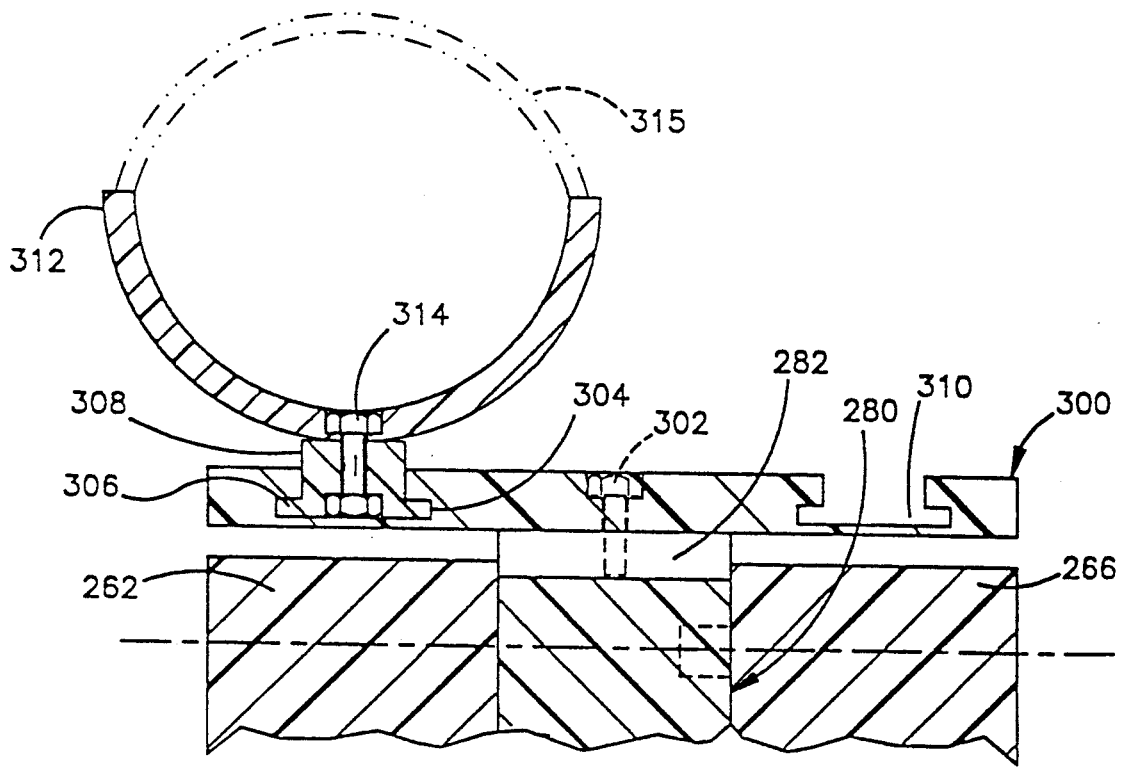
FIG. 13 is an enlarged fragmentary sectional view of a cuff and leg plate portion of the apparatus of FIG. 9.

The index assembly 200 includes a U-shaped index holder 260 (FIGS. 9–11). The index holder 260 has a lower portion 262. A left support arm 264 and a right support arm 266 extend upwardly from the index holder lower portion 262. Two fasteners 268 extend through the index holder lower portion 262 and secure the index holder 260 to an end surface 269 of the table 202, as shown in FIGS. 9 and 10.

A pivot pin 270 (FIGS. 9 and 10) having an axis of rotation 272 extends between the left and right support arms 264 and 266. The axis 272 extends parallel to the plane of the table 202 and in a direction across the width of the table. The pivot pin 270 supports an index disk 280 for pivotal movement relative to the index holder 260. The index disk 280 is disposed between the left and right support arms 264 and 266 of the index holder. The index disk 280 is a part circular structure, shaped somewhat like a piece of pie, having a flat upper end surface 282 and a flat lower end surface 284. An outer circumferential surface 286 extends between the upper and lower end surfaces. A flat left outer side surface 290 and a flat right outer side surface 292 are on opposite sides of the index disk 280.

Two sets of index openings are arrayed on opposite sides of the index disk 280. The first or left set of index openings 294 extend inwardly into the index disk 280 from the left outer side surface 290 of the index disk. The index openings 294 are arrayed in a part circular pattern on the index disk 280 with the axis 272 as the center of the pattern. The index openings 294 are all equally spaced from the axis 272. The index openings 294 are spaced from each other in equal angular increments about the axis 272 and near the outer edge 286 of the index disk 280. In the illustrated embodiment, the index openings 294 are 20' apart from each other, although this spacing could be different as described in more detail below.

The second or right set of index openings 296 extend inwardly into the index disk 280 from the right outer side surface of the index disk. The index openings 296 are arrayed in a part circular pattern on the index disk 280 with the axis 272 as the center of the pattern. The index openings 296 are all equally spaced from the axis 272. The index openings 296 are spaced from each other in equal angular increments about the axis 272 and near the outer axis of the index disk 280. In the illustrated embodiment, the index openings 296 are 20° apart from each other, although this spacing could be different as described in more detail below.

The index openings 294 are staggered from the index openings 296. That is, the index openings 294 on one side of the disk 280 do not align with the index openings 296 on the opposite side of the disk. Instead, the index openings 294 are disposed so as to fall halfway between pairs of index openings 296 of the other set. Thus, there is a 10° angular increment between an index opening 294 of one set and an adjacent index opening 296 of the other set.

A leg plate 300 is fixed to the index disk 280 for movement with the index disk. Three leg plate attachment screws 302 extend through the leg plate 300 and through the upper end surface 282 of the index disk 280, to secure the leg plate to the index disk. The leg plate 300 is long enough to substantially support the lower leg of the patient.

Two slider grooves in the leg plate 300 extend the length of the leg plate. A left slider groove 304 (FIGS. 11, 13) is shaped to receive a tenon portion 306 of a cuff slider 308. A right slider groove 310 extends parallel to the left slider groove 304, also for the length of the leg plate 300. The right slider groove 310 is similarly shaped to receive the tenon portion 306 of the cuff slider 308. The cuff slider 308 is slidable in one or the other of the slider grooves 304 and 306.

A leg cuff 312 is fixed to the slider 308 for movement with the slider. A plurality of cuff attachment screws 314 extend through the cuff 312 into the slider 308 to secure the cuff to the slider. Thus, the cuff 312 is slidable with the slider 308 on the index disk 280. As the index disk pivots about the axis 272, the cuff is free to slide along the upper end surface 282 of the index disk. Two leg straps 315 (FIG. 9) are attached to the leg cuff 312. The straps 315 are wrapped around the lower leg of the patient to secure the lower leg to the cuff 312.

The index assembly 200 includes a left plunger assembly 312 and a right plunger assembly 318, for controlling the pivotal location of the index disk 280.

The left plunger assembly 316 (FIG. 11) includes a left plunger support block 320 fixed to the index holder left support arm 264 by two screw fasteners 322. A left plunger 324 extends through a passage 326 in the left plunger support block 320. The left plunger 324 has a trailing end portion 328 to which is connected a left plunger actuator 330. The left plunger actuator 330 is a cord or string 332 having a handle or finger grip 334 on its end remote from the left plunger 324. The actuator cord 332 extends from the left plunger 324 through the actuator passage 238 (FIG. 9) in the left coil support block 228, to a location where it can be grasped by the patient's left hand.

The left plunger 324 projects from the left plunger support block 320 into the index holder left support arm 264. A body portion 336 of the left plunger 324 is received in a chamber 338 in the index holder left support arm 264. A compression spring 340 is disposed in the chamber 338 between the left plunger support arm 264 and the body portion 336 of the left plunger 324. The compression spring 340 biases the left plunger 324 toward the index disk 280, in a direction to the right as viewed in FIG. 9. A pulling force applied by the patient, through the actuator 330, is sufficient to overcome the biasing effect of the spring 340 and retract the left plunger 324 away from the index disk 280, in a direction to the left as viewed in FIG. 9.

A leading end portion 342 of the left plunger 324 extends from the left plunger body portion 336 toward the index disk 280. The leading end portion 342 is aligned with the track of the left index openings 294 in the index disk 280. Thus, as the index disk 280 pivots about the axis 272, the left index openings 294 sequentially come into position adjacent the left plunger 324 so that the leading end portion 342 of the left plunger can enter into a selected one of the left index openings to block pivotal movement of the index disk. When the leading end portion 342 of the left plunger 324 is not engaged in one of the left index openings 294 in the index disk 280, the leading end portion of the left plunger rides along the left outer side surface 290 of the index disk, between the left index openings.

The right plunger assembly 318 (FIG. 11A) is similar to the left plunger assembly. The right plunger assembly 318 includes a right plunger support block 350 fixed to the index holder right support arm 266 by two screw fasteners 352. A right plunger 354 extends through a passage 356 in the right plunger support block 350. The right plunger 354 has a trailing end portion 358 to which is connected a right plunger actuator 360. The right plunger actuator 360 is a cord or string 362 having a handle or finger grip 364 on its end remote from the right plunger 354. The actuator cord 362 extends from the right plunger 354 through an actuator opening 335 (FIG. 9) in the right coil support block 228, to a location where it can be grasped by the patient's right hand.

The right plunger 354 (FIG. 11A) projects from the right plunger support block 350 into the index holder right support arm 266. A body portion 366 of the right plunger 354 is received in a chamber 368 in the index holder right support arm 266. A compression spring 370 is disposed in the chamber 368 between the right plunger support arm 266 and the body portion 366 of the right plunger 354. The compression spring 370 biases the right plunger 354 toward the index disk 280, in a direction to the left as viewed in FIG. 11A. A pulling force applied by the patient, through the actuator 360, is sufficient to overcome the biasing effect of the spring 370 and retract the right plunger 354 away from the index disk 280, in a direction to the right as viewed in FIG. 9.

A leading end portion 372 of the right plunger 354 extends from the right plunger body portion 366 toward the index disk 280. The leading end portion 372 is aligned with the track of the right index openings 296 in the index disk 280. Thus, as the index disk 280 pivots about the axis 272, the right index openings 296 sequentially come into position adjacent the right plunger 354 so that the leading end portion 372 of the right plunger 354 can enter into a selected one of the right index openings to block pivotal movement of the index disk. When the leading end portion 372 of the right plunger 354 is not engaged in one of the right index openings 296 in the index disk 280, the leading end portion of the right plunger rides along the right outer side surface 292 of the index disk, between the openings.

The index assembly 200 in the illustrated embodiment is constructed for use in magnetic resonance imaging of a knee joint of a patient lying on his back inside a primary imaging coil of a magnetic resonance imaging apparatus. The imaging table 202 is first slid out of the primary coil so the patient can lie down on the table. The secondary coil assembly 206 is opened, by swinging the upper coil portion 218 away from the lower coil portion 216. The patient lies on the table 202 and rests his upper leg on the leg support wedge 250. The lower leg rests on the cuff 312. The patient's knee joint is disposed above the lower portion 216 of the secondary coil. The upper coil portion 218 is then repositioned over the lower coil portion 216 for imaging of the knee joint. The straps 315 are fitted around the lower leg to stabilize the joint and secure the lower leg to the cuff 312. The table 202 is then slid into the primary imaging coil.

The index assembly 200 can be in any desired index position to start. For example, the index assembly 200 can be in the index position shown in solid lines in FIG. 10, in which the leg plate 300 and the cuff 312 extend parallel to the plane of the table 202.

In this starting position, the various elements of the index assembly 200 are in the positions shown in solid lines in FIG. 8 and in FIG. 9. The cuff 312 and the slider 308 are disposed at a relatively distal location (to the left as viewed in FIG. 10) along the leg plate 300. The leading end portion 342 of the left plunger 324 is engaged in a left index opening 380 (FIG. 11) which is one of the plurality of left index openings 294 in the index disk 280. The right plunger 354 is not engaged in any of the plurality of right index openings 296 in the index disk 280—instead, the leading end portion 372 of the right plunger is in abutting engagement with the right outer side surface 292 of the index disk. The engagement of the left plunger 324 in the index disk 280 blocks pivotal movement of the index disk about the pivot pin 270. As a result, the cuff 312 and the lower leg are fixed in position, and a clear image of the knee joint can be taken.

After the knee joint is imaged in this first index position, the patient grasps the left actuator handle 334 and pulls on it. The force of the patient's pulling is transmitted through the actuator cord 332 to the left plunger 324. The left plunger 324 is retracted against the biasing effect of the left plunger spring 340. The leading end portion 342 of the left plunger 324 comes out of the index opening 380 in the index disk 280.

At this point, the left plunger 324 no longer blocks pivotal movement of the index disk 280, and the index disk can move out of the first index position shown in solid lines in FIG. 11. Since the right plunger 354 is not engaged in any of the plurality of right index openings 296 in the index disk 280, the index disk is free to pivot about the axis 272. The weight of the patient's lower leg, pressing down through the cuff 312, the slider 308, and the leg plate 300, causes the index disk 280 to pivot downward in the direction indicated by the arrow 382 in FIG. 10. As the index disk 280 pivots, the leading end portion 372 of the right plunger 354 slides along the right outer side surface 292 of the index disk. The biasing effect of the right plunger spring 370 forces the leading end portion 372 of the right plunger 354 against the outer side surface 292 of the index disk 280.

Once the index disk 280 has pivoted through an angle of 10°, the index opening 384 (FIG. 11A), which is one of the plurality of right index openings 296 in the index disk, becomes aligned with the right plunger 354. The leading end portion 372 of the right plunger 354 moves into the index opening 384. The engagement of the right plunger 354 in the index disk 280 blocks pivotal movement of the index disk 280 about the axis 272. As a result, the cuff 312 and the lower leg are fixed in a second index position, and a clear image of the knee joint can be taken in this second index position, in which the knee joint is moved 10° from the first index position.

Further images can be taken at succeeding 10° index positions, by having the patient actuate the right plunger 354, then the left plunger 324, in succession. Thus, the physician can obtain a more complete picture of the structure and movement of the knee joint through its range of motion.

It can thus be seen that the index assembly 200 is constructed so that, upon patient release of one of the plunges 324 and 354 via its actuator, the index disk 280 will automatically move into the next sequential index position, without skipping any intervening index positions. This ensures accurate and repeatable imaging sequences. If desired, of course, the patient can actuate the index assembly 200 as many times as directed between images, for example to take images at every 20° through the range of motion of the joint rather than every 10°. Imaging at other angular increments can be provided by placing the index openings 294 and 296 in the index disk 280 at different angular spacings, such as 5° rather than 10°, etc.

As the knee joint is flexed (moved from a straighter position to a more bent position), the knee itself tends to rise, thus pulling the lower leg closer toward the secondary coil assembly 206. The sliding movement of the cuff 312 on the index disk 280 accommodates this. As seen in FIG. 10, the cuff 312 is in a more distal position along the index disk 280 when the upper end surface 282 of the index disk is parallel to the plane of the table 202. When the knee joint is flexed and the index disk is moved to the second index position shown in phantom in FIG. 10, the cuff 312 and the slider 308 slide proximally (to the right as viewed in FIG. 10) along the index disk 280. Thus, the knee joint is not strained but instead is allowed to retain its normal configuration.

FIG. 10 illustrates movement of the index disk 280 through an angle of 30° between the position shown in solid lines and the position shown in phantom. This is for purposes of clarity in the drawings. Showing the index disk 280 moved only through a 10° increment, for example, in FIG. 10, would not show the pivotal movement so clearly. Thus, the 30° range of motion shown in FIG. 10 between the first index position shown in solid lines and the second index position shown in phantom would be achieved by indexing three times--left, right, and left.

As noted above, the index holder 260 is secured to the end surface 269 of the table 202. This allows the patient's foot to drop down below the upper major side surface 203 of the table 202, when the index assembly 200 is moved to a low position (past that shown in phantom in FIG. 10). Thus, the knee joint can be moved through a greater range of motion than if the foot could not drop below the upper major side surface 203 of the table 202. Accordingly, the physician can image the knee joint through a greater range of motion.

This mounting of the index assembly on the end of the table provides substantial advantages as compared to prior art imaging in which the patient's entire body remains above the top of the imaging table. A typical imaging table is about 6" deep (tall). Thus, when a patient lies on the top of a table and inside the primary imaging coil, the table takes up 6" of vertical space inside the primary coil, space which can then not be used for imaging. Mounting the index assembly on the end of the table in accordance with the present invention regains this 6" of space, and allows much greater range of imaging motion. The table works for the patient and physician, rather than against them. For example, the knee joint can be imaged through a range of about 60° with the indexing assembly 200, while the prior art images only allow imaging through a range of about 30°.

It should further be noted that the imaging apparatus in accordance with both the first embodiment (FIGS. 1-8) and second embodiment (FIGS. 9-13) allow the patient to lie on his back inside the primary coil. Prior art imaging apparatus for indexing require the patient to lie on his stomach. Since it takes two to five minutes for each image (cut), the patient can be required to lie on his stomach inside a claustrophobic primary coil for 30 to 60 minutes to image a joint with prior art imaging apparatus. This is extremely uncomfortable. The patient's comfort is vastly increased by lying on his back, and the imaging process is consequently improved.

The known secondary coil assembly 206 is offset laterally from the longitudinal center line of the table 202 so that the coil portions 216 and 218 are not over the center line of the table 202 but rather are offset slightly to one side. The secondary coil can be flipped 180° to place the coil portions 216 and 218 offset slightly to the other side of the center of the table 202. Thus, clear images of the knee can be taken with the secondary coil with either the left or right knee joint in its normal position off the centerline of the body. To accommodate this variance in imaging position, the leg plate 300 has both the left slider groove 304 and the right slider groove 310. When the slider 308 is placed in the left slider groove 304, the cuff 312 is in the proper position to image the left knee. When the slider 308 is placed in the right slider groove 310, the cuff 312 is then in the proper position to image the right knee.

As discussed above, the coil support blocks 226 and 228 (FIGS. 9-12) in the second embodiment of the invention raise the secondary coil assembly 206 off its normal position on the table 202. It may be necessary or desirable to set the secondary coil assembly 206 at different heights relative to the table 202. If so, coil support blocks can be provided with different heights to enable setting of the secondary coil assembly 206 at different heights. Also, the leg support wedge 250 can be replaced with similar wedges having different angles and heights, to raise the knee to different heights above the table 202.

From the above description of the invention, those skilled in the art will perceive improvements, changes and modifications in the invention. Such improvements, changes and modifications within the skill of the art are intended to be covered by the appended claims.

I claim:

1. A method of imaging a knee joint of patient with an imaging unit, said method comprising the steps of gripping a lower portion of a patient's leg at a location below the knee joint with a cuff which is connected with a rotatable member, positioning the knee joint in the imaging unit, bending the knee joint while the knee joint is in the imaging unit, moving the lower portion of the patient's leg along an arcuate path while bending the knee joint, rotating the cuff and the member under the influence of force applied against the cuff by the lower portion of the patient's leg and transmitted from the cuff to the member during bending of the knee joint, retaining the lower portion of the patient's leg against movement in a direction transverse to the arcuate path during bending of the knee joint, said step of retaining the lower portion of the patient's leg against movement in a direction transverse to the arcuate path including restraining the lower portion of the patient's leg against movement in a direction transverse to the arcuate path under the influence of force transmitted from the member through the cuff to the lower portion of the patient's leg, and imaging the knee joint when the lower portion of the patient's leg is at each of a plurality of positions along the arcuate path.

2. A method as set forth in claim 1 further including the steps of interrupting bending of the knee joint with the lower portion of the patient's leg at each of the plurality of positions along the arcuate path, and maintaining the lower portion of the patient's leg stationary in each of the plurality of positions in turn while imaging the knee joint.

3. A method as set forth in claim 2 wherein said step of positioning the knee joint in the imaging unit includes positioning the knee joint in the imaging unit with an axis about which the member is rotatable extending through the patient's leg.

4. A method as set forth in claim 1 wherein said step of rotating the cuff and the member includes rotating the cuff and member about an upright axis which extends through the patient's leg, said step of moving the lower portion of the patient's leg along an arcuate path includes moving the lower portion of the patient's leg along a generally horizontal arcuate path.

5. A method as set forth in claim 1 further including the step of moving the cuff relative to the member to change the distance between the cuff and the axis of rotation of the member during performance of said step of moving the lower portion of the patient's leg along an arcuate path while bending the knee joint.

6. A method of imaging a knee joint of a patient while the patient is lying on his or her back, said method comprising the steps of gripping a lower portion of a patient's leg at a location below the knee joint with a cuff which is connected with a rotatable member, positioning the knee joint in the imaging unit with the patient lying on his or her back, bending the knee joint while the knee joint is in the imaging unit and while the patient is lying on his or her back, moving the lower portion of the patient's leg along an arcuate path while bendig the knee joint with the patient lying on his or her back, rotating the cuff and the member about an axis extending through the member during bending of the knee joint while the patient is lying on his or her back, retaining the lower portion of the patient's leg against movement in a direction transverse to the arcuate path during bending of the knee joint while the patient is lying on his or her back, said step of retaining the lower portion of the patient's leg against movement in a direction transverse to the arcuate path including restraining the lower portion of the patient's leg against movement in a direction transverse to the arcuate path under the influence of force transmitted from the member through the cuff to the lower portion of the patient's leg, and imaging the knee joint when the lower portion of the patient's leg is at each of a plurality of positions along the arcuate path while the patient is lying on his or her back.

7. A method as set forth in claim 6 further including the step of moving the cuff along a linear path extending perpendicular to the axis about which the cuff and member are rotatable during bending of the knee joint with the patient lying on his or her back.

8. A method as set forth in claim 7 wherein said step of moving the cuff along a linear path includes moving the cuff along the linear path under the influence of force applied against the cuff by the lower portion of the patient's leg during performance of said step of bending the knee joint while the knee joint is in the imaging unit and while the patient is lying on his or her back.

9. A method as set forth in claim 8 wherein said step of rotating the cuff and the member about an axis extending through the member during bending on the knee joint while the patient is lying on his or her back includes rotating the cuff and the member under the influence of force transmitted from the cuff to the member from the lower portion of the patient's leg.

10. A method as set forth in claim 6 further including the steps of interrupting bending of the knee joint with the lower portion of the patient's leg at each of a plurality of positions along the arcuate path and while the patient is lying on his or her back, and maintaining the lower portion of the patient's leg stationary in each of the plurality of positions in turn while imaging the knee joint with the patient lying on his or her back.

11. A method of imaging a knee joint of patient with an imaging unit, said method comprising the steps of gripping a lower portion of a patient's leg at a location below the knee joint with a cuff which is connected with a rotatable member, positioning the knee joint in the imaging unit, bending the knee joint while the knee joint is in the imaging unit, rotating the cuff and the member about an axis during bending of the knee joint, moving the cuff along a linear path relative to the rotatable member under the influence of force applied against the cuff by the lower portion of the patient's leg while bending the knee joint, and imaging the knee joint when the lower portion of the patient's leg is at each of a plurality of positions in the imaging unit.

12. A method as set forth in claim 11 wherein said step of moving the cuff along a linear path includes moving the cuff toward the axis about which the cuff and rotatable member rotate during bending of the knee joint to flex the patient's leg and moving the cuff away from the axis about which the cuff and rotatable member rotate during bending of the knee joint to extend the patient's leg.

13. A method as set forth in claim 11 further including moving the lower portion of the patient's leg along an arcuate path while bending the knee joint, and retaining the lower portion of the patient's leg against movement in a direction transverse to the arcuate path during bending of the knee joint, said step of retaining the lower portion of the patient's leg against movement in a direction transverse to the arcuate path including restraining the lower portion of the patient's leg against movement in a direction transverse to the arcuate path under the influence of force transmitted from the member through the cuff to the lower portion of the patient's leg.

14. A method as set forth in claim 11 wherein said step of rotating the cuff and member about an axis including moving the cuff and member under the influence of force applied against the cuff by the lower portion of the patient's leg.

15. A method as set forth in claim 11 wherein said step of positioning the knee joint in the imaging unit is performed with the patient lying on his or her back, said steps of bending the knee joint being performed with the patient lying on his or her back, and said step of imaging the knee joint being performed with the patient lying on his or her back.

16. A method as set forth in claim 11 further including the steps of interrupting bending of the knee joint when the lower portion of the patient's leg is at each of the plurality of positions in the imaging unit, and maintaining the lower portion of the patient's leg stationary in each of the plurality of positions in turn while imaging the knee joint.

17. Apparatus for magnetic resonance imaging a knee joint of a patient, said apparatus comprising a magnetic resonance imaging unit, and positioning means for controlling bending of the patient's knee joint with the knee joint in said magnetic resonance imaging unit, said positioning means including a base, a member rotatable relative to said base about an upright axis with said member at least partially in said magnetic resonance imaging unit, cuff means for holding a lower portion of the patient's leg at a location below the knee joint with the knee joint in said magnetic resonance imaging unit and with the patient's leg extending across said member through the upright axis about which said member is rotatable, and connector means for connecting said cuff means with said rotatable member and for rotating said rotatable member under the influence of force transmitted from said cuff means through said connector means to said rotatable member from the lower portion of the patient's leg.

18. An apparatus as set forth in claim 17 wherein said member has a circular configuration and the upright axis about which said member is rotatable extends through the center of said member.

19. An apparatus as set forth in claim 18 wherein said positioning means includes a plurality of index locations disposed along a peripheral edge portion of said member, and means for engaging at least one of said index locations to hold said member against rotation about the upright axis during imaging of the knee joint in said magnetic resonance imaging unit.

20. An apparatus as set forth in claim 17 wherein said positioning means includes surface means disposed in a place extending perpendicular to the upright axis and connected with said member for at least partially supporting the patient's leg during rotation of said member about the upright axis.

21. An apparatus as set forth in claim 17 wherein said connector means and cuff means cooperate to guide movement of the lower portion of the patient's leg along an arc having a center of curvature located on the upright axis about which said member rotates.

22. An apparatus as set forth in claim 17 wherein said positioning means includes an index mechanism for retaining said member and the lower portion of the patient's leg in each index position of a series of index positions in turn, said index mechanism including a plurality of index locations disposed in an arcuate array on said member, retainer means for engaging sad index locations, said retainer means being movable between an extended position engaging an index location and a retracted position spaced from said index locations, biasing means for urging said retainer means toward the extended position, latch means for retaining said retainer means in the retracted position against the influence of said biasing means, said latch means being operable between a latch position in which said latch means is effective to retain said retainer means in the retracted position and a release position in which said latch means is ineffective to retain said retainer means in the retracted position, and means for operating said latch means from the latch position to the release position in response to rotational movement of said member about the upright axis.

23. An apparatus for magnetic resonance imaging a knee joint of a patient, said apparatus comprising a magnetic resonance imaging unit, and positioning means for controlling bending of the patient's knee joint with the knee joint in said magnetic resonance imaging unit, said positioning means including a base, a member rotatable relative to said base with said member at least partially in said magnetic resonance imaging unit, cuff means for holding a lower portion of a patient's leg at a location below the knee joint with the knee joint in said magnetic resonance imaging unit, and connector means for connecting said cuff means with said member, said connector means including means for enabling said cuff means to move relative to said member along a linear path in one direction during rotation of said member and flexion of the knee joint and for enabling said cuff means to move relative to said member along the linear path in a direction opposite to the one direction during rotation of said member and extension of the knee joint, said cuff means being movable relative to said member along the linear path under the influence of force transmitted to said cuff means from the lower portion of the patient's leg.

24. An apparatus as set forth in claim 22 wherein said connector means includes surface means for forming a linear track connected with said member and a slider movable along the linear track and connected with said cuff means.

25. An apparatus as set forth in claim 25 wherein said connector means transmits force from said cuff means to rotate said member under the influence of force applied against said cuff means by the lower portion of the patient's leg.

26. An apparatus as set forth in claim 25 wherein said positioning means includes means for supporting said member for rotation about a horizontal axis.

27. An apparatus as set forth in claim 25 wherein said positioning means includes a plurality of index locations disposed along a peripheral edge portion of said member, and means for engaging at least one of said index locations to hold said member against rotation during imaging of the knee joint in said magnetic resonance imaging unit.

28. An apparatus for magnetic resonance imaging a knee joint of a patient, said apparatus comprising a magnetic resonance imaging unit, and positioning means for controlling bending of the patient's knee joint in said magnetic resonance imaging unit, said positioning means including a base, a member rotatable relative to said base with said member at least partially in said magnetic resonance imaging unit, cuff means for holding a lower portion of a patient's leg at a location below the knee joint with the knee joint in said magnetic resonance imaging unit, connector means for connecting said cuff means with said member, an arcuate array of index locations connected with said rotatable member, said arcuate array of index locations having a center of curvature disposed on an axis about which said member is rotatable, an index element movable between an engaged position engaging at least one of said index locations to retain said member against rotation and a disengaged position spaced from said index location to release said member for rotation, biasing means for urging said index element toward the engaged position, and actuator means for moving said index element from the engaged position to the disengaged position against the influence of said biasing means and under the influence of force applied to said actuator means by the patient.

29. An apparatus as set forth in claim 28 further including connector means for enabling said cuff means to move relative to said member along a linear path in one direction during rotation of said member and flexion of the knee joint and for enabling said cuff means to move relative to said member along the linear path in a direction opposite to the one direction during rotation of said member and extension of the knee joint, said cuff means being movable relative to said member along the linear path under the influence of force transmitted to said cuff means from the lower portion of the patient's leg.

30. An apparatus as set forth in claim 28 wherein said connector means includes means for rotating said rotatable member under the influence of force transmitted from said cuff means through said connector means to said rotatable member from the lower portion of the patient's leg.

31. An apparatus as set forth in claim 30 further including means for supporting said member for rotation about an upright axis which extends through the patient's leg.

32. An apparatus as set forth in claim 30 further including means for supporting said member for rotation about a horizontal axis.

* * * * *

UNITED STATES PATENT AND TRADEMARK OFFICE
CERTIFICATE OF CORRECTION

PATENT NO. : 5,329,924
DATED : July 19, 1994
INVENTOR(S) : Peter M. Bonutti

It is certified that error appears in the above-indentified patent and that said Letters Patent is hereby corrected as shown below:

Column 15, line 27, change "bendig" to --bending--.

Column 17, line 23, change "place" to --plane--.

Column 17, line 38, change "sad" to --said--.

Column 18, line 9, change "22" to --23--.

Column 18, line 14, change "25" to --23--.

Column 18, line 19, change "25" to --23--.

Column 18, line 22, change "25" to --23--.

Signed and Sealed this

Fifth Day of December, 1995

BRUCE LEHMAN

*Attest:*

*Attesting Officer*   Commissioner of Patents and Trademarks